US011213348B2

(12) United States Patent
Kachaamy

(10) Patent No.: US 11,213,348 B2
(45) Date of Patent: Jan. 4, 2022

(54) SPHINCTEROTOME DEVICE AND METHODS AND USES THEREOF

(71) Applicant: International Private Bank LLC, Christiansted, VI (US)

(72) Inventor: Toufic Kachaamy, Phoenix, AZ (US)

(73) Assignee: International Private Bank LLC, Christansted (VG)

( * ) Notice: Subject to any disclaimer, the term of this patent is extended or adjusted under 35 U.S.C. 154(b) by 0 days.

(21) Appl. No.: 16/640,044

(22) PCT Filed: Aug. 31, 2018

(86) PCT No.: PCT/US2018/049240
§ 371 (c)(1),
(2) Date: Feb. 18, 2020

(87) PCT Pub. No.: WO2019/046802
PCT Pub. Date: Mar. 7, 2019

(65) Prior Publication Data
US 2020/0375656 A1    Dec. 3, 2020

Related U.S. Application Data

(60) Provisional application No. 62/553,726, filed on Sep. 1, 2017.

(51) Int. Cl.
*A61B 18/14* (2006.01)
*A61B 17/00* (2006.01)
(Continued)

(52) U.S. Cl.
CPC .... *A61B 18/1492* (2013.01); *A61B 17/00234* (2013.01); *A61M 25/0071* (2013.01);
(Continued)

(58) Field of Classification Search
CPC .......... A61B 18/1492; A61M 25/0071; A61M 25/09
See application file for complete search history.

(56) References Cited

U.S. PATENT DOCUMENTS

| 5,024,617 A | 6/1991 | Karpiel |
| 9,179,969 B2 | 11/2015 | Martinez |

(Continued)

FOREIGN PATENT DOCUMENTS

| CN | 204246239 U | 4/2015 |
| CN | 104955412 A | 9/2015 |

(Continued)

OTHER PUBLICATIONS

International Search Report and Written Opinion received in PCT Application No. PCT/US2018/049240, dated Oct. 29, 2018.

(Continued)

*Primary Examiner* — Linda C Dvorak
*Assistant Examiner* — Bo Ouyang
(74) *Attorney, Agent, or Firm* — Katten Muchin Rosenman LLP

(57) ABSTRACT

A sphincterotome device can be used to achieve appropriate positioning within the biliary duct during cannulation. The sphincterotome device enables performance of a "double-wire" or multiple wire procedure without the need for removal and reintroduction of the sphincterotome device, thereby allowing for a shorter procedure.

23 Claims, 8 Drawing Sheets

(51) Int. Cl.
*A61M 25/00* (2006.01)
*A61M 25/09* (2006.01)

(52) U.S. Cl.
CPC ... *A61M 25/09* (2013.01); *A61B 2017/00323* (2013.01); *A61B 2017/00818* (2013.01); *A61B 2018/144* (2013.01); *A61M 2025/091* (2013.01)

(56) References Cited

U.S. PATENT DOCUMENTS

| | | | | |
|---|---|---|---|---|
| 2003/0060842 | A1* | 3/2003 | Chin | A61B 17/3478 606/170 |
| 2012/0310265 | A1* | 12/2012 | Martinez | A61B 18/1492 606/170 |
| 2013/0158507 | A1* | 6/2013 | Brown | A61M 25/0028 604/506 |
| 2014/0350463 | A1 | 11/2014 | Nahon et al. | |

FOREIGN PATENT DOCUMENTS

| | | | | |
|---|---|---|---|---|
| CN | 204723173 U | 10/2015 | | |
| WO | 2014137600 A1 | 9/2014 | | |
| WO | WO-2014137600 A1 * | 9/2014 | | A61F 2/011 |

OTHER PUBLICATIONS

Notification of the First Office Action dated Aug. 27, 2021, from Chinese Office Action No. 201880055945.X, 10 sheets.

* cited by examiner

SPHINCTEROTOME DEVICE AND METHODS AND USES THEREOF

CROSS-REFERENCE OF RELATED APPLICATIONS

This application is the U.S. National Phase under 35 U.S.C. § 371 of International Patent Application No. PCT/US2018/049240, filed on Aug. 31, 2018, which in turn claims the benefit of U.S. Provisional Application No. 62/553,726, filed on Sep. 1, 2017 the entire disclosures of which Applications are incorporated by reference herein for all purposes.

TECHNICAL FIELD

The present description relates in general to medical devices, and more particularly to, for example, without limitation, sphincterotome devices, methods and uses thereof.

BACKGROUND OF THE DISCLOSURE

An estimated 1,230,000 endoscopic retrograde cholangiopancreatography ("ERCP") procedures were performed in the 28 member countries of the European Union and the United States in 2016. As part of an ERCP procedure, cannulation must first be achieved in order to gain access to the desired duct(s); however, this can sometimes be challenging. One approach is to use a sphincterotome device (also called a papillotome), inserted through a working channel of a duodenoscope. A sphincterotome is a catheter that contains an electrosurgical cutting wire at the distal end, which is used to perform sphincterotomies (i.e., cutting of sphincter muscles in order to gain duct access to perform follow-up procedures).

The description provided in the background section should not be assumed to be prior art merely because it is mentioned in or associated with the background section. The background section may include information that describes one or more aspects of the subject technology.

Figure 1:
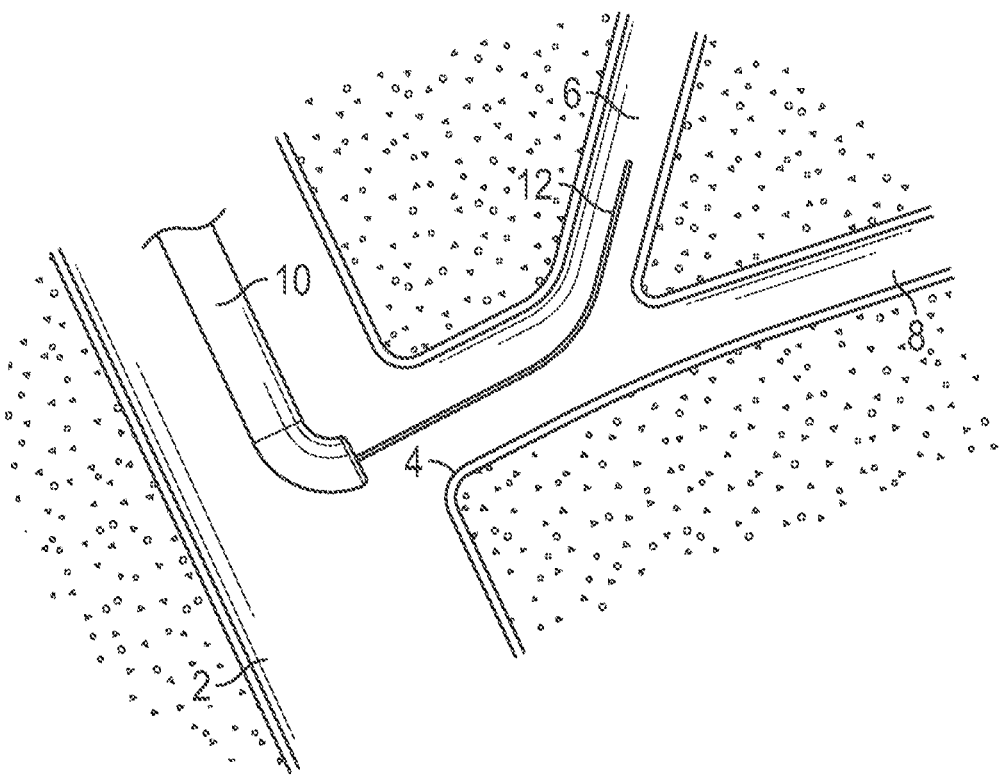
FIG. 1 illustrates a diagram of a stage of a biliary cannulation procedure using a sphincterotome device.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

An exemplary embodiment of a sphincterotome device of the present disclosure can be used to achieve appropriate positioning within the biliary duct during cannulation. The common biliary duct splits into left and right hepatic ducts, and an exemplary sphincterotome device of the present disclosure may help with accessing these ducts more easily. In some cannulation procedures, high obstruction of the biliary tree may require the placement of two guidewires. In order to place the two wires, a sphincterotome device might need to be taken out of one duct after the first wire is placed, which then allows a second wire to be placed. An example embodiment of the present disclosure allows both wires to be placed without the need for removal of the sphincterotome, thus shortening the procedure.

In some embodiments of the present disclosure, an exemplary sphincterotome device makes the "double-wire" technique easier to perform, as it would allow manipulation of the biliary duct while at the same time manipulating the second wire to direct it into the bile duct. When a guidewire or the sphinctertome are inserted into the pancreatic duct, it may facilitate the second wire entry into the bile duct but blocking the pancreatic duct or stretching the biliary duct, thus making it easier to access the biliary duct with the second wire. In some instances, it is more difficult to pass a wire through the biliary duct when the catheter is pushed into it as it may fold the duct leading to blocking the passage of the wires.

One or more embodiments of the present disclosure may include various advantages during a "double-wire" or "multiple wire" technique. For example, some embodiments may allow for a shorter procedure because there is no need to remove the sphincterotome device and reintroduce it again over the first guidewire; the second guidewire may be inserted immediately and is positioned in such a way that it may enter the biliary duct. Additionally, one or more embodiments of the present disclosure may reduce the risk of post-ERCP pancreatitis because there would be a lesser need for the often-difficult manipulation of two guidewires to achieve correct angulation and avoid the possibility of leaving a wire in the pancreatic duct for a longer time.

Accordingly, embodiments of the present disclosure may achieve advantages such as shorter and easier endoscopic retrograde cholangiopancreatographies, for example, involving patients with challenging ductal anatomies. Additionally, embodiments of the present disclosure may lead to higher successful cannulation rates; a reduced risk of post-ERCP pancreatitis; increased safety by reducing the need for more invasive procedures; and the ability to conserve time, devices, and resources when performing further intrahepatic procedures after biliary cannulation.

Referring now to FIGS. 1-4, an example of a biliary cannulation procedure is illustrated along with the use of a sphincterotome device. In some procedures, a guidewire 12 can be inserted through the lumen of a sphincterotome 10, which extends through the duodenum 2 to the location of a sphincter 4 (i.e., sphincter of Oddi) at the major duodenal papilla. The guidewire 12 is then manipulated to achieve biliary duct cannulation into the biliary duct 6, as shown in FIG. 1.

Figure 2:
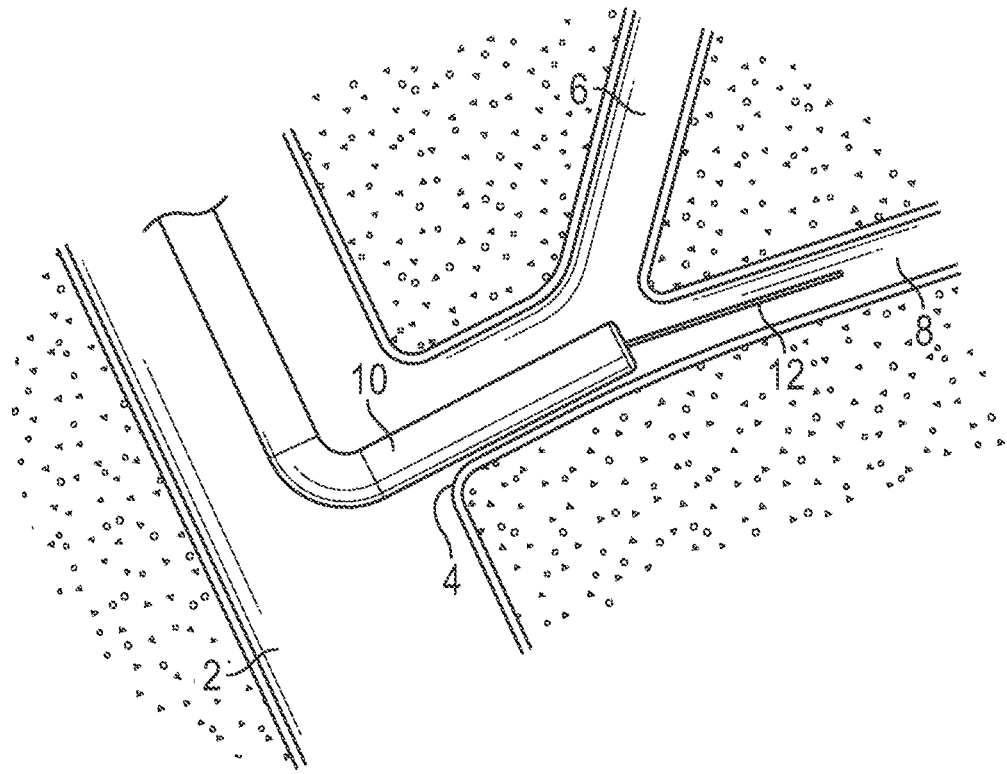
FIG. 2 illustrates a diagram of another stage of the biliary cannulation procedure using a sphincterotome device.
Figure 3:
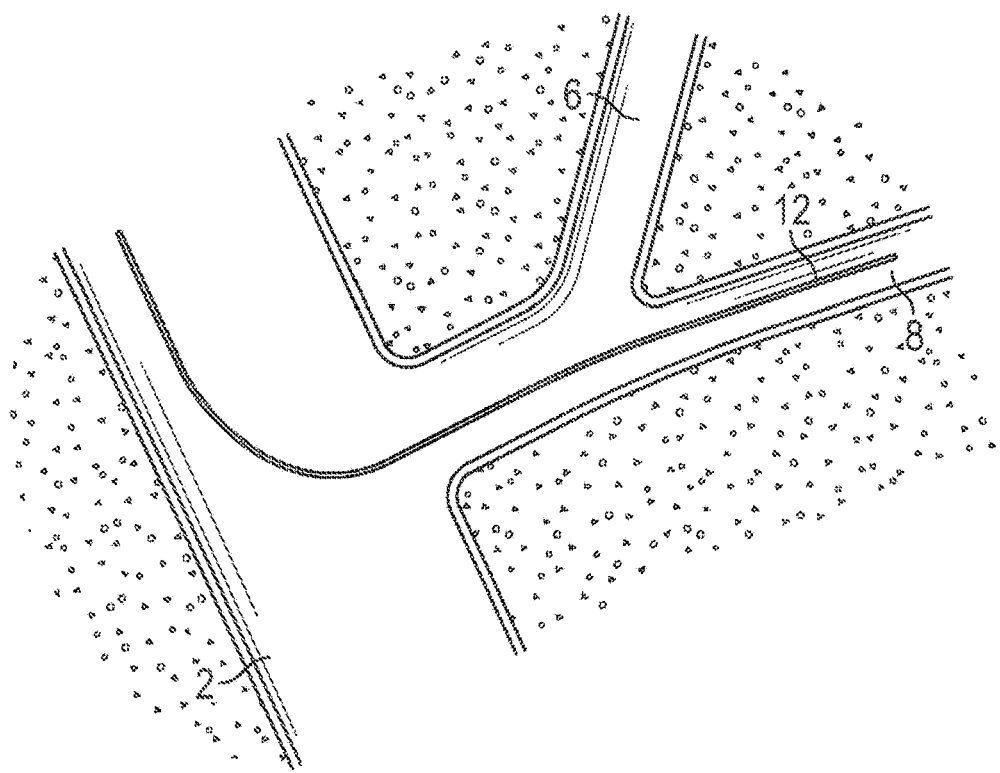
FIG. 3 illustrates a diagram of another stage of the biliary cannulation procedure using a sphincterotome device.
Figure 4:
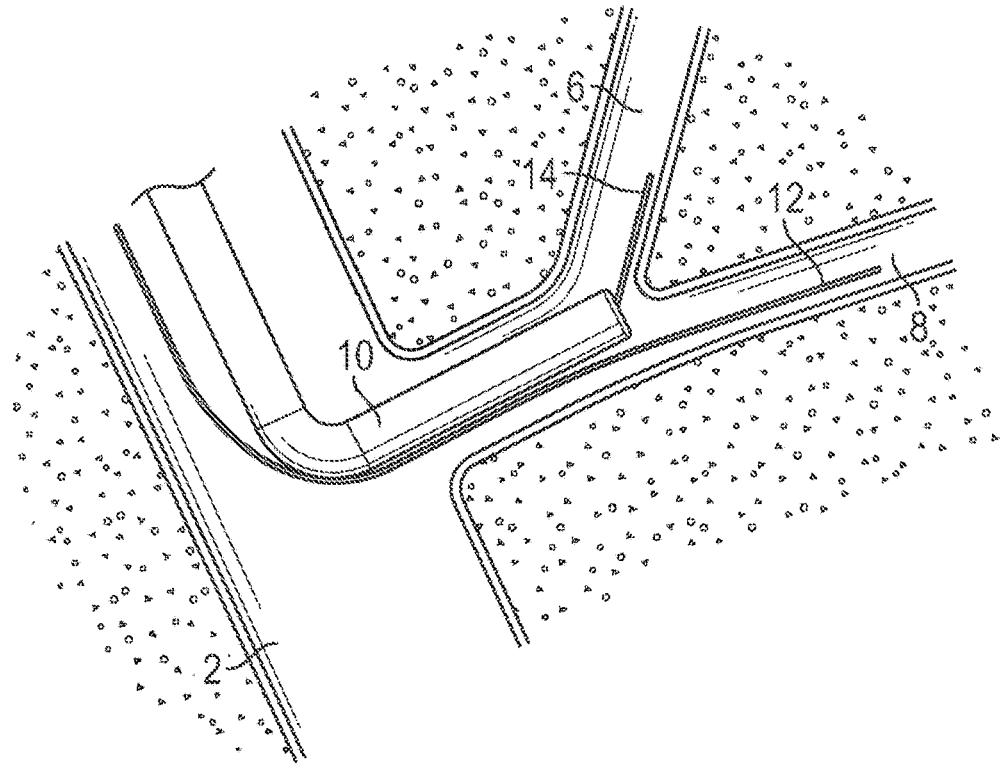
FIG. 4 illustrates a diagram of another stage of the biliary cannulation procedure using a sphincterotome device.

In some procedures, it can also be challenging to reach the biliary duct 6, in which case the guidewire 12 may be placed in the pancreatic duct 8 instead, as shown in FIG. 2. In this scenario, a "double-wire" technique can be used so that more aggressive and risky techniques can be avoided. As shown in FIG. 3, in an exemplary double-wire technique, the first guidewire 12 is left in the pancreatic duct 8, the sphincterotome is withdrawn. As shown in FIG. 4, a second guidewire 14 is inserted into the sphincterotome 10. The sphincterotome 10 is inserted next to the first guidewire 12 in order to enter the biliary duct 6 more easily, as shown in FIG. 4. In some instances, contrast dye may be injected through the sphincterotome 10 to confirm such placement.

To reduce operation complexity and duration, a sphincterotome device can be provided with features that facilitate entry into both the pancreatic duct and the biliary duct. An example of such a device is shown in FIGS. 5-9. While these figures illustrate different features, it will be understood that the features can be implemented together or alternatively.

Figure 5:
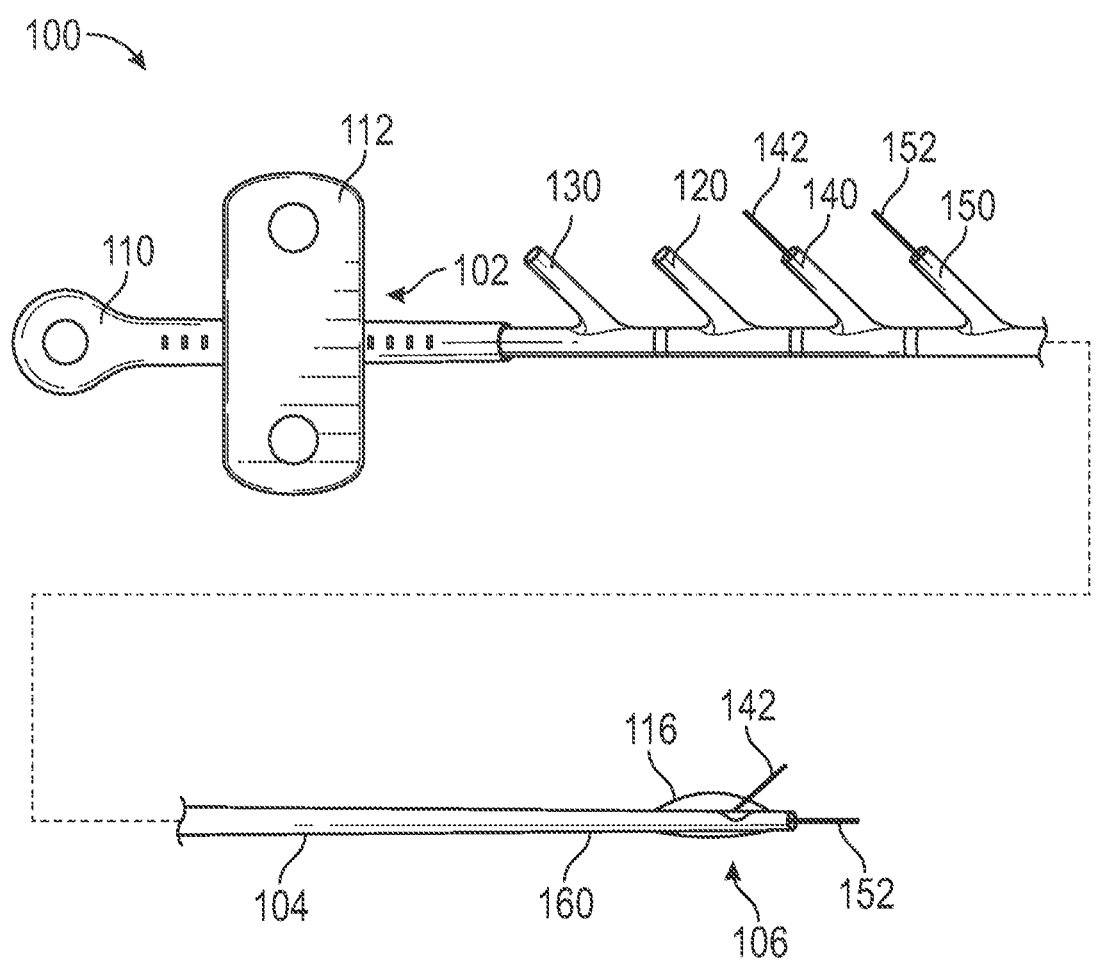
FIG. 5 illustrates a plan view of an example of a sphincterotome device.

As shown in FIG. 5, a sphincterotome 100 can include a proximal portion 102 for operation by a user and a distal portion 106 for insertion into a patient. At the proximal portion 102, various features can be provided for interaction by a user to operate the distal portion 106. For example, a handle 110 and a slider 112 can be provided for actuating a cutting wire 116 at the distal portion 106. The cutting wire 116 can be retracted and/or extended based on movement of the slider 112 relative to the handle 110. By moving the cutting wire 116, the distal portion 106 can be deflected relative to a middle portion 104 of the shaft 160 of the sphincterotome 100, as discussed further herein. The cutting wire 116 may comprise a conductor. For example, the cutting wire 116 may be formed from a conductive metal that can be electrified during cutting (e.g., for heating), if desired.

The proximal portion can further include one or more infusion ports. A proximal fluid entry port 120 at the proximal portion 102 is provided in fluid communication with a proximal fluid exit port at the distal portion 106. Fluid can be provided at the proximal fluid entry port 120 for infusion at the distal portion 106 by way of a lumen extending there between, as discussed further herein. A distal fluid entry port 130 at the proximal portion 102 is provided in fluid communication with a distal fluid exit port at the distal portion 106. Fluid can be provided at the distal fluid entry port 130 for infusion at the distal portion 106 by way of a lumen extending there between, as discussed further herein.

The proximal portion can further include one or more ports for controlling guidewires. A proximal guidewire entry port 140 at the proximal portion 102 is provided with a proximal guidewire 142 extending therein and toward the distal portion 106. A distal guidewire entry port 150 at the proximal portion 102 is provided with a distal guidewire 152 extending therein and toward the distal portion 106. The proximal guidewire 142 and the distal guidewire 152 can exit the distal portion 106 at different locations and/or angles to provide access and entry into different areas of the body.

Figure 6:
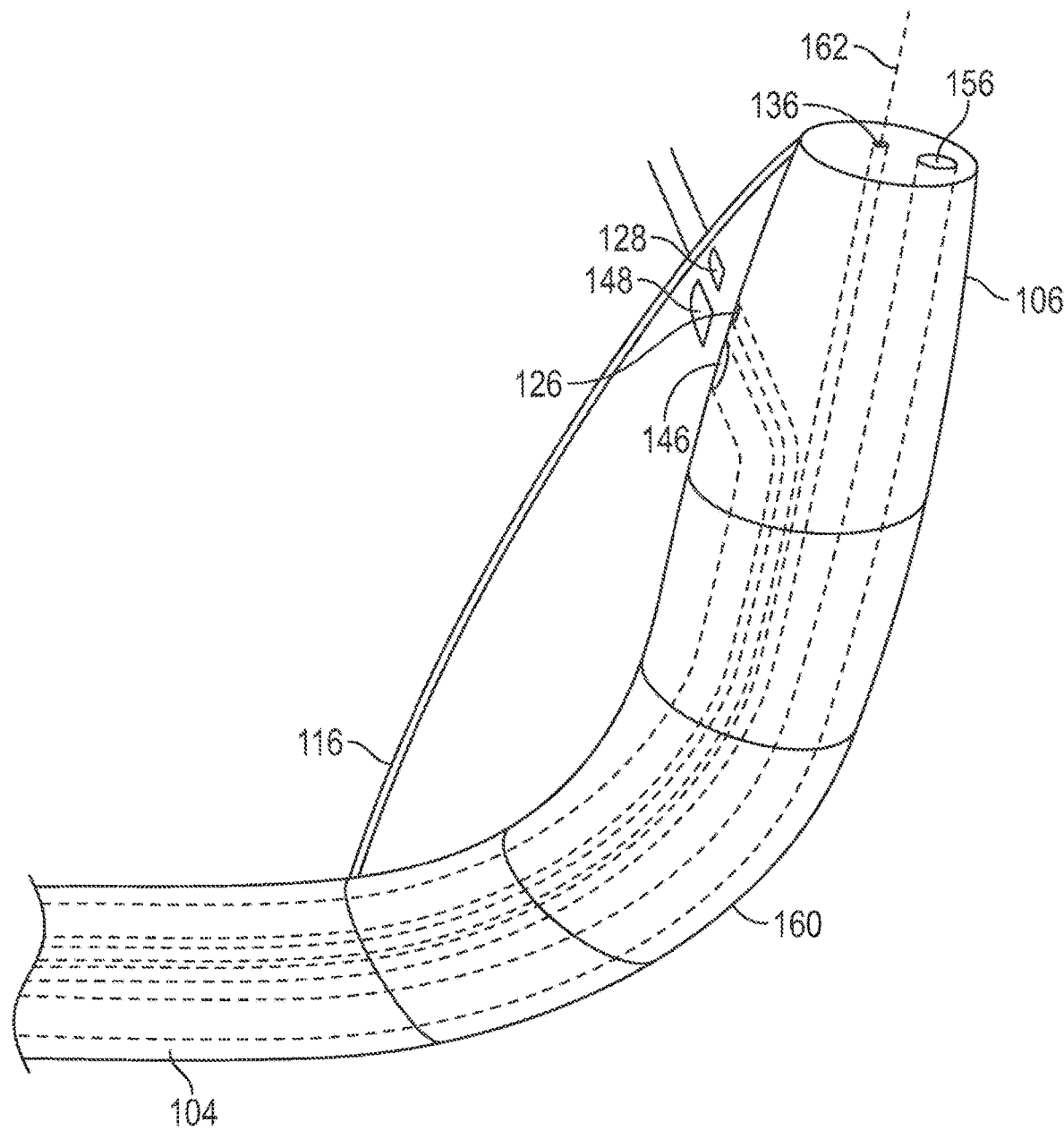
FIG. 6 illustrates a perspective view of a distal end portion of a sphincterotome device.
Figure 7:
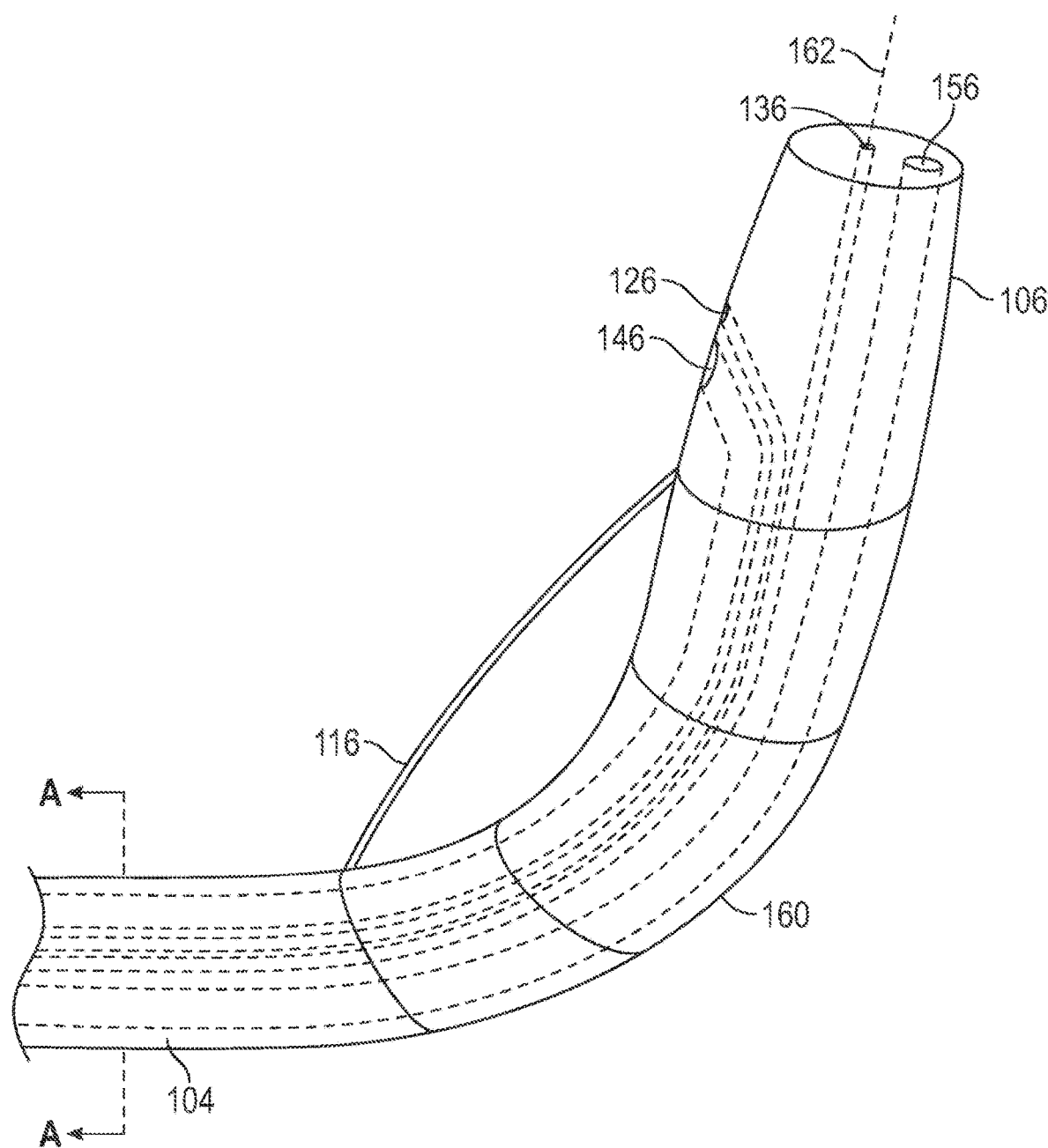
FIG. 7 illustrates a perspective view of a distal end portion of a sphincterotome device.

FIGS. 6 and 7 illustrate embodiments and various components of the sphincterotome 100. A shaft can be rotatable to change the position of the distal end of the sphincterotome. A shaft can include multiple lumens. In the depicted example, five lumens are provided. At the distal portion, each lumen can terminate to provide access for fluid or other devices. Lumens may be used to convey guidewires, which correspond to the proximal and distal guidewire lumens. Two more lumens may be used for contrast injection, which correspond to proximal and distal injection ports. In some embodiments, the proximal guidewire and injection lumens/ports may be fused into one. The sphincterotome device of the present disclosure also may contain one lumen for a cutting wire. The distal tip of an exemplary sphincterotome shaft may be 5 millimeters long and pre-curved in some embodiments. The diameter of an exemplary sphincterotome shaft may be approximately 7 Fr, but could also be smaller. In some embodiments, the sphincterotome shaft of the present disclosure may be compatible with standard duodenoscopes that include a 4.2 millimeter working channel, although this description is not limiting to that effect.

As shown in FIG. 6, a distal guidewire exit port 156 can be used with the distal guidewire 152. The distal guidewire exit port 156 can be on the distalmost tip of the shaft 160. The distal guidewire exit port 156 can be used to direct the distal guidewire 152 into the pancreatic or biliary duct. In this way, pancreatic duct entry stretches the bile duct, thus facilitating second guidewire insertion through the proximal guidewire exit port 146 into the biliary duct without need to withdraw the shaft 160. If biliary cannulation is achieved at first attempt using the distal guidewire 152, the shaft 160 can be left in place for appropriate positioning and further intrahepatic manipulation.

As further shown in FIGS. 6 and 7, a proximal guidewire exit port 146 can be used with the proximal guidewire 142. The proximal guidewire exit port 146 can be on a cutting wire side of the shaft 160, e.g., approximately 0.2 to 0.25 inches (approximately 0.5 to 1.0 centimeters) away from the distalmost tip of the shaft 160. In some embodiments, the proximal guidewire 142 is inserted into the proximal guidewire exit port 146 if a first attempted biliary cannulation using the distal guidewire 152 is unsuccessful. The proximal guidewire exit port 146 is oriented at an oblique angle 148 with respect to a central axis 162 of the shaft 160. Such an angle can be 20-80°, 40-80°, 50-70°, or about 60°. The angle can be selected to align with the bile duct anatomy of a patient to facilitate biliary cannulation. The proximal guidewire exit port 146 can also be used for contrast injection to confirm placement of the proximal guidewire exit port 146.

As further shown in FIGS. 6 and 7, a distal fluid exit port 136 can be located on the distalmost tip of the shaft 160. The distal fluid exit port 136 can be used for contrast injection, which facilitates placement of the distal guidewire 152. The distal fluid exit port 136 can optionally be aligned with the central axis 162 of the shaft 160.

As further shown in FIGS. 6 and 7, a proximal fluid exit port 126 can be located proximal to the distalmost end of the shaft 160. The proximal fluid exit port 126 can be used for contrast injection, which facilitates placement of the proximal guidewire 142. The proximal fluid exit port 126 can be on a cutting wire side of the shaft 160, e.g., approximately 0.2 to 0.25 inches (approximately 0.5 to 1.0 centimeters) away from the distalmost tip of the shaft 160. The proximal fluid exit port 126 is oriented at an oblique angle 128 with respect to a central axis 162 of the shaft 160. Such an angle can be 20-80°, 40-80°, 50-70°, or about 60°. The angle 128 can be selected to align with the bile duct anatomy of a patient to facilitate biliary cannulation. The angle 128 can be the same as or different from the angle 148.

As further shown in FIGS. 6 and 7, one or more cutting wires such as a cutting wire 116 can be placed within a cutting wire lumen and attached near a distal end of the shaft 160. An exposed portion of the cutting wire 116 can be approximately 0.1 inch or 20 to 30 millimeters long and positioned on a radial side of the shaft. The cutting wire 116 can be pulled to bend the distal portion 106 of the shaft 160, and the flexibility allows the sphincterotome device to accommodate a wider range of individual patient anatomies. The cutting wire 116 can extend outside the shaft 160 to connect to an end (FIG. 6) distal to the proximal guidewire exit port 146 and/or the proximal fluid exit port 126 or to a portion of the shaft 160 that is proximal to the proximal guidewire exit port 146 and/or the proximal fluid exit port 126 (FIG. 7). It will be recognized that other placements of the cutting wire 116 can be selected to providing bending as desired.

Figure 8:
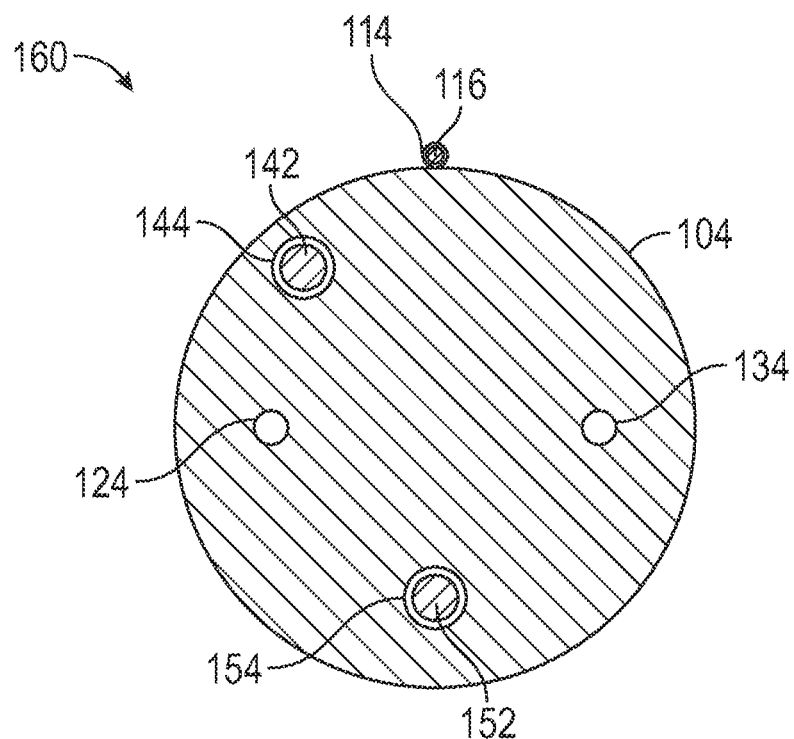
FIG. 8 illustrates a sectional view of the sphincterotome device of FIG. 7 taken along line A-A.

FIG. 8 illustrates an example of a design of a sphincterotome device. In some embodiments, and illustrated in FIG. 8, the cutting wire 116 is positioned at about 12 o'clock relative to a transverse cross-section of the shaft 160 and within a cutting wire lumen 114. The proximal guidewire lumen 144 is at about 11 o'clock relative to a transverse cross-section of the shaft 160 (e.g., about 30° from or within 45° from the cutting wire 116). The circumferential offset of the proximal guidewire lumen 144 and the cutting wire lumen 114 allows the cutting wire 116 and the proximal guidewire 142 to exit at different circumferential locations at the distal portion of the shaft 160. The sphincterotome 100 of FIG. 8 can also contain a distal guidewire lumen 154 and/or two contrast injection lumens: a proximal fluid lumen 124 and a distal fluid lumen 134. The proximal fluid lumen 124 fluidly connects the proximal fluid entry port 120 with the proximal fluid exit port 126. The distal fluid lumen 134 fluidly connects the distal fluid entry port 130 with the distal fluid exit port 136. Thus, in the exemplary embodiment of FIG. 8, the sphincterotome device can include five lumens: two for contrast injection, two for guidewires, and one for the cutting wire.

In some embodiments, for 0.025-inch guidewires, the lumens for the proximal and distal guidewires may be approximately the same size (i.e., in diameter). Use of a 0.025-inch wire for the first guidewire, in the event the first guidewire enters the pancreatic duct, is less likely to cause pancreatitis than would a larger wire. Moreover, such smaller guidewires can be advanced further and become more stable and are almost as stable as 0.035-inch wires. In some embodiments, the external diameter of the sphincterotome device should not be larger than 7 Fr, and will depend on the exact engineering/design of the sphincterotome device. Thus, having 0.025 inch wires may help decrease the total outer diameter of the sphincterotome device. Other diameters of wire may also be used to achieve a similar result, and this description is not meant to be limiting with respect to other feasible wire sizes.

In some embodiments, the proximal exit ports on the side of the shaft are placed 0.5 to 1.0 centimeters away from the tip of the sphincterotome device. Positioning of the proximal exit ports at other distances with respect to the tip of the sphincterotome device may provide similar results. Regardless, in some embodiments, the guidewire can exit the sphincterotome device at an angle relative to the sphincterotome device at 60°. In some patients, the biliary tract is angled at 30-40° with respect to the pancreatic duct, and with appropriate movement of an exemplary sphincterotome device of the present disclosure, cannulation of a greater number of patients can be achieved with an angle of 50-70° (e.g., approximately 60°). Other angles, greater than or less than 60°, can be used to achieve a similar result.

Figure 9:
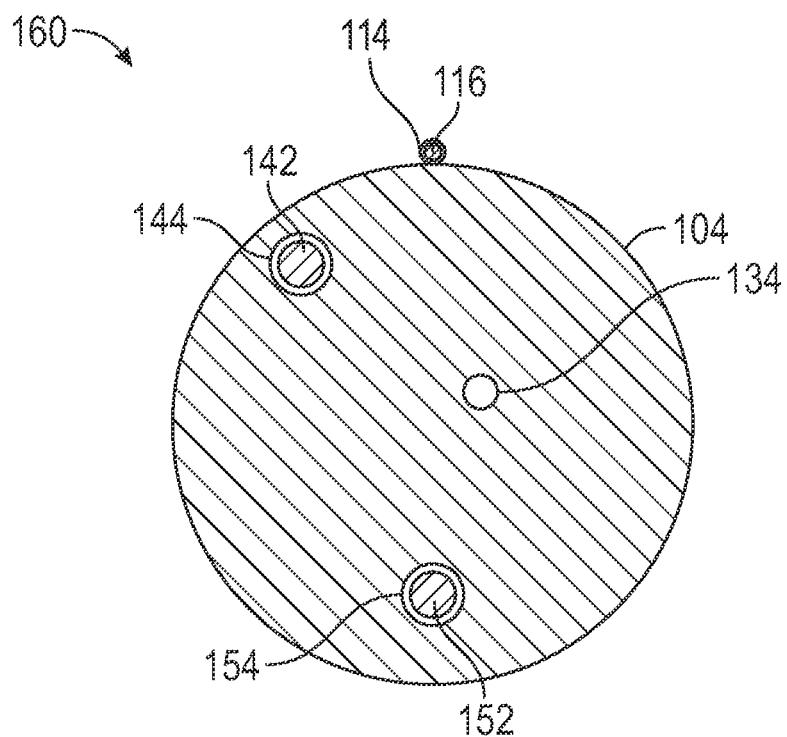
FIG. 9 illustrates a sectional view of an alternative sphincterotome device.

FIG. 9 illustrates another example of a design of a sphincterotome device. While some features are the same as the design illustrated in FIG. 8, it will be understood that a smaller number of fluid lumens can be included. For example, the sphincterotome 100 of FIG. 8 can include only one contrast injection lumen, such as the distal fluid lumen 134. Alternatively, the sole lumen can be the proximal fluid lumen 124. Thus, in the exemplary embodiment of FIG. 9, the sphincterotome device has four lumens in total: one for contrast injection, two for guidewires (one of which can also be used for contrast injection) and one for the cutting wire.

Although the examples of FIGS. 6-9 show lumens 114, 144, and 154 as each accommodating a single wire (e.g., a cutting wire, a first guidewire, and a second guidewire respectively), it should be appreciated that any or all of lumens 114, 144, 154 can accommodate more than one wire at the same time or at different times (e.g., by providing guidewires or cutting wires that are smaller in cross-sectional diameter than those shown in the noted figures or by providing lumens 114, 144, and/or 154 that are larger in cross-sectional diameter than those shown).

Moreover, it should be appreciated that any or all of lumens 114, 144, 154, 124, and/or 134 can be provided with a wire (e.g., a cutting wire or a guidewire) therein or a wire and/or one or more other suitable medical devices can be provided separately from, and later inserted into and/or removed from or through the lumen. For example, in some scenarios, the sphincterotome 100 can be used to deliver two or more wires to a cavity (e.g., a fluid collection, or an abscess) to secure access to place multiple devices such as stents or dilators, or to obtain one or more samples such as fluid samples or tissue samples.

Figure 10:
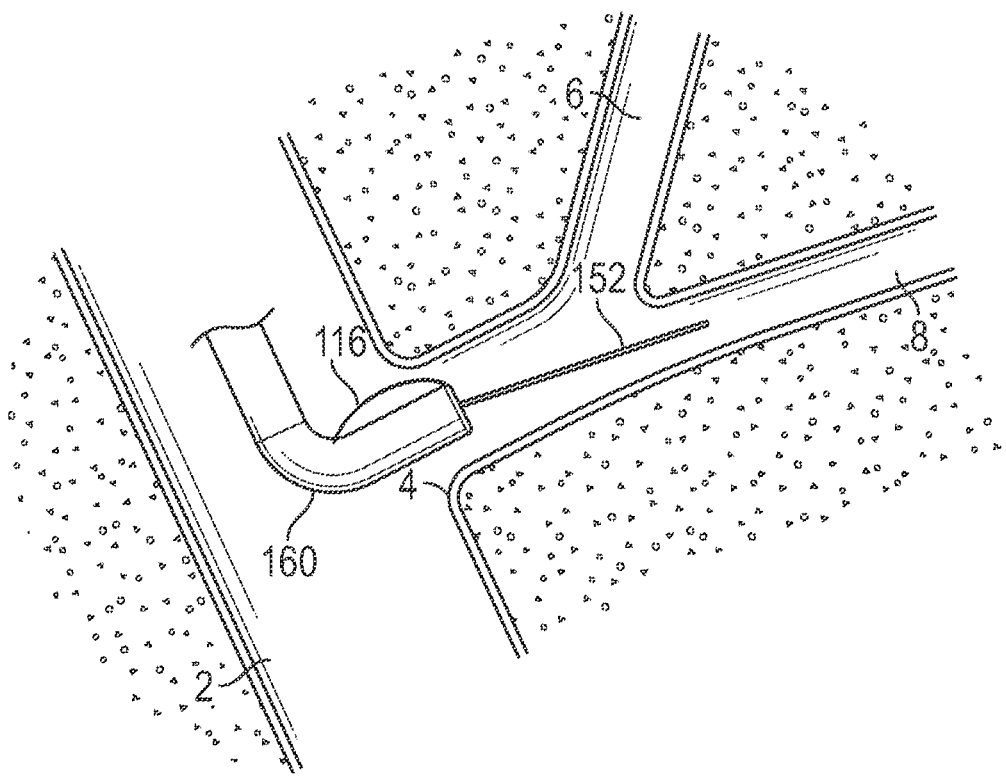
FIG. 10 illustrates a diagram of a stage of a biliary cannulation procedure using a sphincterotome device.
Figure 11:
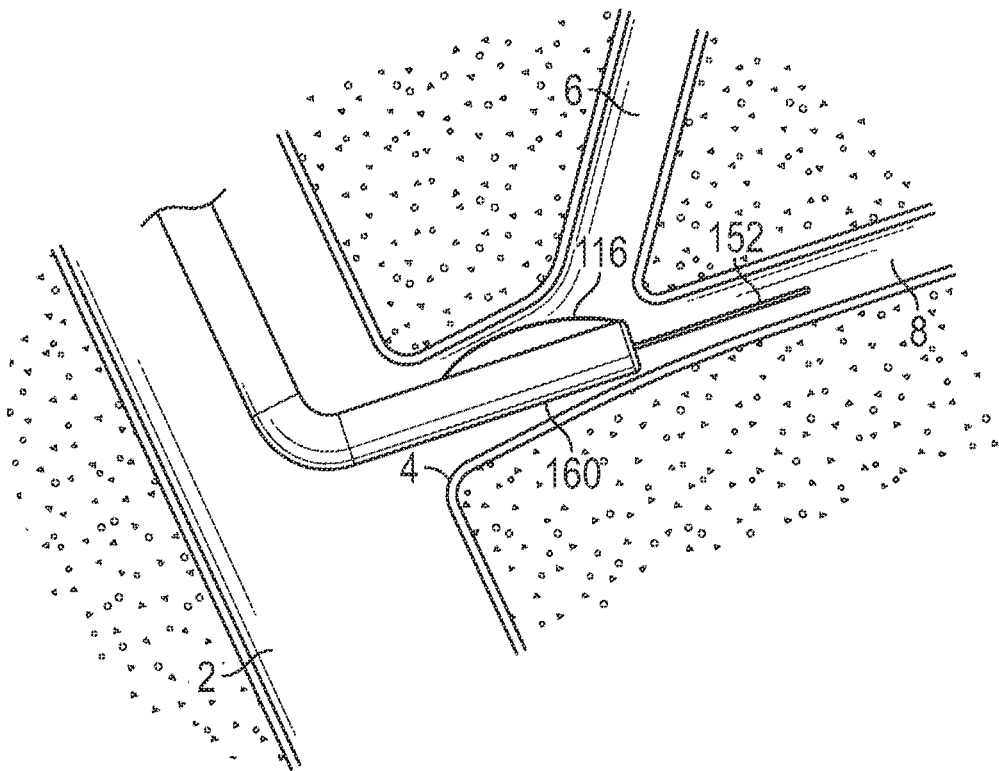
FIG. 11 illustrates a diagram of another stage of the biliary cannulation procedure using a sphincterotome device.
Figure 12:
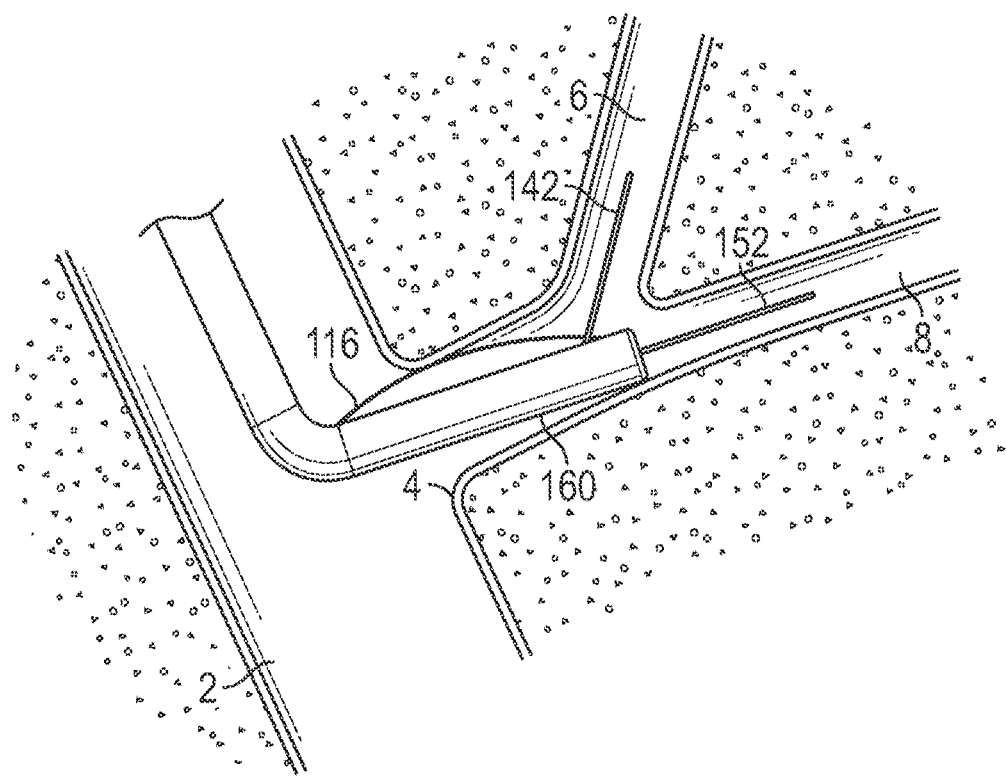
FIG. 12 illustrates a diagram of another stage of the biliary cannulation procedure using a sphincterotome device.

Referring now to FIGS. 10-12, an example of a biliary cannulation procedure is illustrated along with the use of a sphincterotome device.

As shown in FIG. 10, a shaft 160 of a sphincterotome can be provided through a duodenum 2 to the location of a sphincter 4 (i.e., sphincter of Oddi) at the major duodenal papilla. Access can be facilitated by use of a duodenoscope (not shown) in concert with the sphincterotome. The distal guidewire 152 and/or the shaft 160 is advanced to achieve cannulation into either the biliary duct 6 or the pancreatic duct 8. In some cases, cannulation with the distal guidewire 152 is achieved into the pancreatic duct 8, rather than the biliary duct 6. Injection of contrast can be performed to verify the position of the distal guidewire 152.

As shown in FIG. 11, the distal guidewire 152 can be maintained within the pancreatic duct 8, and the shaft 160 can be advanced over the distal guidewire 152 to align with the biliary duct 6. In particular, proximal exit ports of the shaft 160 can be positioned axially and on a radial side of the shaft 160 to align with the biliary duct 6.

As shown in FIG. 12, the proximal guidewire 142 can be extended out of a guidewire exit port to achieve cannulation into the biliary duct 6. Based on the position and orientation of the guidewire exit port, the extension of the proximal guidewire 142 should be aligned with the position and orientation of a pathway into the biliary duct 6. Injection of contrast can be performed to verify the position of the proximal guidewire 142.

Additional procedures can be performed after or during cannulation. For example, the cutting wire 116 can be actuated to bend a distal portion of the shaft 160 as desired. The shaft 160 and/or the cutting wire 116 can maneuver within or otherwise act on nearby anatomy. By further example, the sphincterotome can cut sphincter muscles of the biliary duct with the cutting wire 116. An endoscopic retrograde cholangiopancreatography can be performed on the patient.

By further example, the shaft 160 can be withdrawn while maintaining the proximal guidewire 142 within the biliary duct 6. Additionally or alternatively, the shaft 160 can be withdrawn while maintaining the distal guidewire 152 within the pancreatic duct 8. Other tools and/or devices can be advanced, operated, and/or withdrawn over or along the proximal guidewire 142 and/or the distal guidewire 152. By way of additional examples, additional wires can be used in conjunction with the sphincterotome for other procedures such as dilation or stent procedures or obtaining a tissue sample.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

In one aspect, a term coupled or the like may refer to being directly coupled. In another aspect, a term coupled or the like may refer to being indirectly coupled.

Terms such as top, bottom, front, rear, side, horizontal, vertical, distal, proximal, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for".

The title, background, brief description of the drawings, abstract, and drawings are hereby incorporated into the disclosure and are provided as illustrative examples of the disclosure, not as restrictive descriptions. They are submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirements of the applicable patent law, nor should they be interpreted in such a way.

What is claimed is:

1. A sphincterotome device comprising a shaft extending from a proximal end to a distal end along a longitudinal axis thereof, the shaft comprising:
    a first lumen that extends from the proximal end to a first segment of the distal end along the longitudinal axis, the first lumen comprising at least one cutting wire, the at least one cutting wire exposed along an outer surface along the distal end and emerging from the first lumen at a first exit port and re-entering the first lumen at a first entry port;
    a second lumen that extends from the proximal end to the distal end along the longitudinal axis, the second lumen comprising a second exit port positioned along a side wall of a second segment of the distal end and configured to receive at least a first guidewire; and
    a third lumen that extends from the proximal end to the distal end along the longitudinal axis, the third lumen comprising a third exit port positioned at a tip of a third segment of the distal end and configured to receive at least a second guidewire,
    wherein the first lumen and the second lumen are disposed with a 30° circumferential offset in a cross-section of the shaft to configure the first guidewire and the cutting wire to exit at different circumferential locations on the shaft at the distal end,
    wherein the third lumen is diametrically opposed to the first lumen along the cross-section of the shaft to bend the second guidewire in a direction consistent with the cutting wire, and
    wherein the longitudinal axis, a second longitudinal axis of the first lumen, and a third longitudinal axis of the third lumen are in vertical alignment along the cross-section of the shaft.

2. The sphincterotome device according to claim 1, wherein: the shaft is rotatable to change a direction of the distal end, and the first entry port is positioned distal to the second exit port and is spaced about <2 cm from the distal end.

3. The sphincterotome device according to claim 1, wherein the first entry port is positioned proximal to the second exit port.

4. The sphincterotome device according to claim 1, wherein the second lumen contains at least the first guidewire.

5. The sphincterotome device according to claim 1, wherein the second exit port is configured such that at least the first guidewire exits the second exit port at a 50°-70° angle relative to the longitudinal axis.

6. The sphincterotome device according to claim 1, wherein the third exit port is configured such that at least the second guidewire exits the third exit port at an angle parallel to the longitudinal axis.

7. The sphincterotome device according to claim 1, further comprising a fourth lumen that extends from the proximal end to the distal end parallel to the longitudinal axis, the fourth lumen comprising a fourth exit port, the fourth exit port configured to receive contrast dye and positioned at a tip of the third segment of the distal end near the third exit port, wherein:
    the at least one cutting wire comprises a conductor,
    the shaft is comprised of materials with varying rigidity along the longitudinal axis,
    the fourth exit port is positioned at a tip of the third segment of the distal end near the third exit port.

8. The sphincterotome device according to claim 1, further comprising a handle that is operably connected to the shaft.

9. The sphincterotome device of claim 1, further comprising a fifth lumen that extends from the proximal end to the distal end along the longitudinal axis, the fifth lumen comprising a fifth exit port, the fifth exit port is configured to receive a contrast dye, wherein the fifth port is positioned along a side wall of a second segment of the distal end near the second exit port.

10. The sphincterotome device according to claim 1, wherein the shaft is circular in a vicinity of the first exit port and in a vicinity of the second exit port.

11. A sphincterotome device comprising a shaft extending from a proximal end to a distal end along a longitudinal axis thereof, the shaft comprising:
    a first lumen that extends from the proximal end to a first segment of the distal end along the longitudinal axis, the first lumen comprising at least one cutting wire, the at least one cutting wire exposed along an outer surface along the distal end and emerging from the first lumen at a first exit port and re-entering the first lumen at a first entry port;
    a second lumen that extends from the proximal end to the distal end along the longitudinal axis, the second lumen comprising a second exit port positioned along a side wall of a second segment of the distal end and configured to receive at least a first guidewire; and
    a third lumen that extends from the proximal end to the distal end along the longitudinal axis, the third lumen comprising a third exit port positioned at a tip of a third segment of the distal end and configured to receive at least a second guidewire,
    and wherein the first lumen and the second lumen are disposed with a circumferential offset in a cross-section of the shaft to configure the first guidewire and the cutting wire to exit at different circumferential locations on the shaft at the distal end and the third lumen is diametrically opposed to the first lumen along the cross-section of the shaft to bend the second guidewire in a direction consistent with the cutting wire.

12. The sphincterotome device according to claim 11, wherein the first entry port is positioned proximal to the second exit port.

13. The sphincterotome device according to claim 11, wherein the first entry port is positioned distal to the second exit port.

14. The sphincterotome device according to claim 11, wherein the first entry port is spaced about 0.5 to about 2 cm from the distal end.

15. The sphincterotome device according to claim 11, wherein the second exit port is spaced about 0.5 to about 1 cm from the distal end.

16. The sphincterotome device according to claim 11, wherein the second lumen receives a contrast dye.

17. The sphincterotome device according to claim 11, wherein the third lumen contains at least the second guidewire.

18. The sphincterotome device according to claim 11, wherein the second exit port is configured such that at least the first guidewire exits the second exit port at an angle relative to the longitudinal axis.

19. The sphincterotome device according to claim 11, wherein the third exit port is configured such that at least the second guidewire exits the third exit port at an angle parallel to the longitudinal axis.

20. The sphincterotome device according to claim 11, wherein the at least one cutting wire comprises a conductor.

21. The sphincterotome device according to claim 11, further comprising a handle that is operably connected to the shaft.

22. A method of positioning a sphincterotome device comprising ordered steps of:
    positioning a duodenoscope to allow viewing of a sphincter of the patient;
    providing the sphincterotome device, wherein the sphincterotome device has a shaft comprising:
        a first lumen that extends from the proximal end to a first segment of the distal end along the longitudinal axis, the first lumen comprising at least one cutting wire, the at least one cutting wire exposed along an outer surface along the distal end and emerging from the first lumen at a first exit port and re-entering the first lumen at a first entry port;
        a second lumen that extends from the proximal end to the distal end along the longitudinal axis, the second lumen comprising a second exit port positioned along a side wall of a second segment of the distal end and configured to receive at least a first guidewire; and
        a third lumen that extends from the proximal end to the distal end along the longitudinal axis, the third lumen comprising a third exit port positioned at a tip of a third segment of the distal end and configured to receive at least a second guidewire,
        wherein the first lumen and the second lumen are disposed with a 30° circumferential offset in a cross-section of the shaft to configure the first guidewire and the cutting wire to exit at different circumferential locations on the shaft at the distal end,
        wherein the third lumen is diametrically opposed to the first lumen along the cross-section of the shaft to bend the second guidewire in a direction consistent with the cutting wire, and
        wherein the longitudinal axis, a second longitudinal axis of the first lumen, and a third longitudinal axis of the third lumen are in vertical alignment along the cross-section of the shaft;
    inserting the distal end of the sphincterotome device into a working channel of the duodenoscope;
    inserting at least the second guidewire into the third lumen and through the third exit port;
    verifying that the second guidewire has exited the third exit port positioned at the tip of the third segment of the distal end and has been inserted into a pancreatic duct;
    inserting at the first guidewire into the second lumen and through the second exit port; and
    verifying that the first guidewire has exited the second exit port positioned along the side wall of the second segment of the distal end and has been inserted into the biliary duct.

23. The method according to claim 22, further comprising:
    cutting sphincter muscles of the biliary duct with the at least one cutting wire; and
    performing an endoscopic retrograde cholangiopancreatography on the patient.

* * * * *